(12) United States Patent
Qin

(10) Patent No.: US 8,044,098 B2
(45) Date of Patent: Oct. 25, 2011

(54) USE OF HYDROXYBENZOIC ACIDS AND THEIR ESTERS AND ANALOGUES FOR PREVENTING OR TREATING VIRUS INFECTION

(75) Inventor: Weihua Qin, Guangzhou (CN)

(73) Assignee: Shenghua Guangzhou Pharmaceutical Science & Technology Co., Ltd., Guangzhou (CN)

( * ) Notice: Subject to any disclaimer, the term of this patent is extended or adjusted under 35 U.S.C. 154(b) by 720 days.

(21) Appl. No.: 12/024,833

(22) Filed: Feb. 1, 2008

(65) Prior Publication Data

US 2008/0119550 A1    May 22, 2008

Related U.S. Application Data

(63) Continuation-in-part of application No. PCT/CN2006/001792, filed on Jul. 21, 2006, and a continuation-in-part of application No. PCT/CN2006/001791, filed on Jul. 21, 2006.

(30) Foreign Application Priority Data

Aug. 2, 2005  (CN) .......................... 2005 1 0012287
Aug. 2, 2005  (CN) .......................... 2005 1 0012288

(51) Int. Cl.
   *A61K 31/235*   (2006.01)
   *A61K 9/00*   (2006.01)
(52) U.S. Cl. ........................ 514/544; 424/400
(58) Field of Classification Search .................... 514/544
   See application file for complete search history.

(56) References Cited

U.S. PATENT DOCUMENTS

| | | | | |
|---|---|---|---|---|
| 5,795,911 A | * | 8/1998 | Cheng et al. | .................... 514/456 |
| 6,284,289 B1 | | 9/2001 | Van den Berghe | |
| 6,294,186 B1 | | 9/2001 | Beerse | |
| 6,855,341 B2 | * | 2/2005 | Smith | .......................... 424/642 |

FOREIGN PATENT DOCUMENTS

| | | |
|---|---|---|
| CN | 1162461 A | 10/1997 |
| CN | 1167567 A | 12/1997 |
| CN | 1411339 A | 4/2003 |
| JP | 09059151 * | 3/1997 |

OTHER PUBLICATIONS

JP 09059151 Machine translation, 1997.*
Kane et al. Methyl gallate, Methyl-3,4,5-trihydroxy-benzoate, is a potent and highly specific inhibitor of herpes simplex virus in vitro. II. Antiviral activity of methyl gallate and its derivatives, Bioscience Reports, 1988, vol. 8, No. 1, pp. 95-102.*

Kong, Gengxing et al., "Study of the Anti-HBsAg/HBeAg Component in Canarium Album Raeush," *Journals of Guangzhou Liberation Army High Specialized School*, 1998, 26 (2):5-7.
Chen, Fubiang et al., "The Correlation Between Human Papillomavirus and Cervical Erosion for Carcinogenesis," *China J Cancer Prev Treat*, 2001, 8 (4): 342-344.
Xu, Chenkang et al., "Screening of Human Papillom Virus Infection in Cervix and its Significance," *Journal of Zhongshan Medical University*, 1998, 19 (3): 223-226.
Ahn W.S. et al, "Effect of Retinoic Acid on HPV Titration and Colposcopic Changes in Korean Patients With Dysplasia of the Uterine Cervix," *J. Cell Biochem. Suppl.*, 1997; 28-29: 133-139.
Sun, He et al., "Study on the relationship between the cervical erosion and the herpes simplex virus infection in Xingjiang Uighur and Han nationality women," *China Practical Gynaecology and Obstetrics Journal*, 2001, 17 (7):407-409.
Jiang, Ping et al., "Synthesis of Iso-Butyl Gallate Under Microwave Irradiation," *Chemistry & Industry of Forest Products*, 2005, 25(B10), 113-115.
Li, S. Q., "Research of Synthesis of Octyl Gallate," *Hangzhou Chemical Industry*, 2002, 32(1), 25-26.
Ling, Cuixia et al., "Synthesis of Gallicacid n—Butyl Ester Catalyzed by Magnetic Nanograde Solid Super Acid," *Chemical Industry Times*, 2006, 20(1), 25-26, 35.
Zeng, Yucai et al., "Progress on Synthesis of p—Hydroxybenzoic Esters and Research of Friendly Catalyst in Esterification," *Guangzhou Chemical Industry and Technology*, 2005, 33(6), 13-17.
Yu, Shanxin et al., "Research Progress on Synthesis of Nipagin Esters," *Advances in Fine Petrochemicals*, 2002, 3(1), 42-45.
Berge, Stephen M. et al., "Pharmaceutical Salts," *J. Pharm. Sci.*, 66, 1-19 (1977).
Tan, Xinhua et al., "The Suppressor Effect of Yugan Capsule on the 2.2.15 Cell Secreting HBsAg & HBeAg," *Chinese Journal of Integrated Traditional and Western Medicine on Liver Diseases*, 2004, 14(3): 158.
International Search Report for PCT/CN2006/001792 dated Oct. 26, 2006, 4 pages.
Kane, CJ et al., "Methyl gallate, methyl-3,4,5-trihydroxybenzoate, is a potent and highly specific inhibitor of herpes simplex virus in vitor. II. Antiviral activity of methyl gallate and its derivatives," *Biosci-Rep.* Feb. 1988;8(1):95-102.
Zheng, Shumin et al., "The Relationship of Cervical Cancer with Pathogen Infectious, Cytokine and Se," *Chinese J. Exp Clin Virol.*, 2002, vol. 16, No. 2, pp. 179-183.
International Search Report for PCT/CN2006/001791 dated Oct. 26, 2006, 3 pages.
Li, Xiaoling et al., "Research of biology effect of gallic acid," *China Pharmacist* 2004, vol. 7, No. 10, pp. 767-769.

* cited by examiner

*Primary Examiner* — Shengjun Wang
(74) *Attorney, Agent, or Firm* — Jun He Law Offices P.C.; Zhaohui Wang

(57) ABSTRACT

This invention provides hydroxybenzoic acids, their esters and analogues thereof that are useful for the prevention and/or treatment of virus infection such as HBV, papillomavirus and/or herpes virus infection.

23 Claims, No Drawings

USE OF HYDROXYBENZOIC ACIDS AND THEIR ESTERS AND ANALOGUES FOR PREVENTING OR TREATING VIRUS INFECTION

CROSS-REFERENCE TO RELATED APPLICATIONS

The present application is a continuation-in-part of International Patent Application No. PCT/CN2006/001792 filed on Jul. 21, 2006, which claims priority to Chinese Patent Application No. 200510012287.0 filed on Aug. 2, 2005, and International Patent Application No. PCT/CN2006/001791 filed on Jul. 21, 2006, which claims priority to Chinese Patent Application No. 200510012288.5 filed on Aug. 2, 2005, all of which are incorporated herein by references in their entirety.

TECHNICAL FIELD

This invention is related to the use of hydroxybenzoic acids, their esters and analogues thereof for the prevention and/or treatment of virus infection.

TECHNICAL BACKGROUND

Among hydroxybenzoic acids and their esters, p-hydroxybenzoic acids and their esters are often used as food and drug preservatives. Gallic acid esters can inhibit the synthesis of thromboxane A2 (TXA2). It has a stronger and faster effect against platelets aggregation than aspirin and has been used in solution for injection. Gallic acid has been proven to inhibit hepatitis B virus replication (see *Journals of Guangzhou Liberation Army High Specialized School*, 1998, 26 (2):5-7).

Chinese Patent No. 1411339A and U.S. Pat. No. 6,294,186 disclosed an antimicrobial composition. The composition includes a safe and effective amount of benzoic acid analogues, which have the following structure (II):

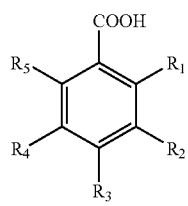

Wherein, $R_1$, $R_2$, $R_4$ and $R_5$ were independently H, OH, F, I, Br, Cl, SH, $NH_2$, CN, alkyl, alkoxy, $NR_2$, OR, $NO_2$, COR, $CONR_2$, $CO_2R$ or $SO_3R$, wherein R was independently H, alkyl or alkoxy; $R_3$ was independently H, OH, F, I, Br, Cl, SH, CN, alkyl, alkoxy, OR, $NO_2$, COR, $CONR_2$, $CO_2R$ or $SO_3R$, wherein R was independently H, alkyl or alkoxy. The aforesaid patent references also pointed out the most preferred embodiment as salicylic acid ("2-hydroxybenzoic acid"), benzoic acid or their combination; they also limited the pH range in which these compounds could be used to 1-7.

Although viruses are the smallest known pathogenic microorganisms, they spread most widely. Today, almost three quarters of contagious diseases in the world are caused by viruses. In clinical diagnosis, many diseases are related to virus infection.

Papillomavirus is a DNA virus that infects the skin or mucosal surfaces of humans or animals. Condyloma acuminata, also called genital warts or venereal warts, is a benign skin mucosa growth induced by human papillomavirus (HPV). It is one of the most frequently seen sexually transmitted diseases and is closely related to inflammation and cancer of the genital organs. Currently, podophyllotoxin is one of the drugs for treating genital warts. Its advantage is short treatment time and disadvantage is skin irritation and severe side effects, including pain, edema, erosion and so on. Recombinant interferon α-2β gel is recognized as an effective external drug to treat genital warts.

Recent researches indicated that 29.3% of the patients of cervical erosion were tested HPV positive while the positive rate among the normal population is only 11.1% (Fuqiang Chen, *Tumor Prevention Magazine*, 2001, 8 (4): 342-344; Chenkang Xu, *Journal of Zhongshan Medical University*, 1998, 19 (3): 223-226). It was reported that the high-risk HPV16, HPV18 were expressed in about 69% of chronic cervicitis patients and that these subtypes were detected at an increasing rate as the degree of the cervical erosion increased (Ahn ws et al, *J. Cell Biochem. Suppl.*, 1997; 28-29: 133-139). The difference of the detection rates of HPV16 and HPV18 between granular or papillary erosion and normal cervix was significant. The positive rate of HPV16 and HPV18 in cervix cancer could be as high as 83.33% when detected by PCR. The DNA of high risk HPV could integrate into the chromosomes of the host cells and then produce E6 and E7 tumor proteins. E6 and E7 could respectively inhibit anti-cancer genes p53 and Rb. As a result, cells would lose the control of p53 and Rb. This would cause cells in the steady state to grow actively and might become cancerous. If HPV16 remains in the cells, it could turn the cervix pathological changes into cancer. Different from the pudendum infection, cervix HPV infection mainly involves HPV 16/18 and usually will not cause warts. It can exist as latent infection for a long time and induce atypical hyperplasia at first and become cancerous when the other factors add on.

Herpes viruses are a virus family with many virus subtypes. Herpes simplex virus (HSV) is one of the most common subtypes of herpes viruses. HSV is a double stranded DNA virus and can enter into target organisms through mouth, respiratory passage, genital tract mucosa, broken skin and many other channels. HSV are further divided into two sub-subtypes, HSV-1 and HSV-2. It is a quite common infection among humans and the infection rate is as high as 80~90%. Typical symptoms include clusters of blisters on certain parts of the mucosa and skin, while occasionally serious systemic disease may occur and do harm to the internal organs. Previous researches indicated that HSV-1 and HSV-2 might separately be related to lip cancer, vulva cancer and cervix cancer and lots of attentions have been drawn to them (Sun He et al., *China Practical Gynaecology and Obstetrics Journal*, 2001, 17 (7):407-409). Presently, drugs for treating HSV infection include idoxuridine, cytosine arabinoside, vidarabine, bromovinyl uridine, acyclovir and so on. But the treatment time of these drugs are quite long, about 5-7 days.

Varicella zoster virus (VZV), also called herpes zoster, is another commonly found herpes virus. VZV is closely related to HSV and shares much genome homology. Initial VZV infection may cause chicken pox, which in a few rare cases, may result in encephalitis or pneumonia. After the initial infection, VZV could remain in the host's nervous system in a latent state. In about 10-20% of cases, VZV reactivates later in the life of the host to cause shingles and related complications.

Antiviral drugs useful for treating hepatitis B virus (HBV) infection, such as vidarabine, vidarabine phosphate, acyclovir and zidovudine, which were tested in the 1980s, were not used to treat hepatitis B anymore due to severe side effects and high toxicity. Recently, many nucleoside drugs, such as Lamivudine, famciclovir, lobucavir, adefovir, FTC, FMAU, FDDC, BMS 200475 and so on, were developed and they had significant inhibiting effect on HBV. Unfortunately, viruses may mutate and become drug resistant after long term use of these drugs. Furthermore, these drugs need to be taken for a long time because short term use only has temporary effect.

There is a continuing need for new drugs useful for the prevention and/or treatment of virus infection such as HBV, papillomavirus and herpes virus infection.

SUMMARY OF THE INVENTION

This invention provides hydroxybenzoic acids, their esters and analogues thereof that are useful for the prevention and/or treatment of virus infection such as HBV, papillomavirus and/or herpes virus infection.

In an embodiment, the present invention provides a method of killing or reducing the amount of virus in a sample by contacting such sample with an effective amount of a compound of the invention.

In another embodiment, the present invention provides a method of treating, alleviating or preventing virus infection or related diseases in a subject by administering to the subject a pharmaceutically effective amount of a pharmaceutical composition comprising a compound of the invention.

DETAILED DESCRIPTION OF THE INVENTION

This invention provides in certain embodiments compounds useful for the prevention and/or treatment of virus infection such as HBV, papillomavirus and herpes virus infection and diseases related thereto in humans and animals.

Provided in certain embodiments are compounds having the structures of Formula (I):

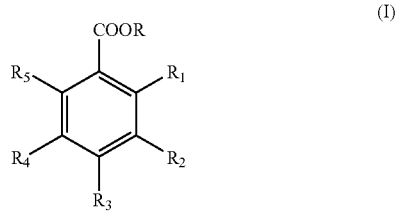

(I)

Wherein, R is hydrogen or $C_{1-12}$ alkyl; $R_1$, $R_2$, $R_3$, $R_4$, $R_5$ are independently hydrogen, halogen, hydroxyl, mercapto, $C_{1-6}$ alkyl, $C_{2-6}$ alkenyl, $C_{2-6}$ alkynyl, $C_{1-6}$ alkoxy, $C_{1-6}$ alkyl-(C=O)—, $C_{1-6}$ alkoxycarbonyl, $C_{3-6}$ cycloalkyl, $C_{3-6}$ cycloalkyl-methyl, $C_{2-6}$ heterocycloalkyl, $C_{2-6}$ heterocycloalkyl-methyl, $C_{6-10}$ aryl (including substituted aryl), $C_{6-10}$ aryloxy, $C_{5-10}$ heteroaryl (including substituted heteroaryl), or $C_{5-10}$ heteroaryloxy, and at least one of $R_1$, $R_2$, $R_3$, $R_4$, and $R_5$ is hydroxyl.

In an embodiment of the present invention, R is hydrogen, $R_3$ is hydroxyl, and $R_1$, $R_2$, $R_4$, $R_5$ are as defined above. In a preferred embodiment, R is hydrogen, $R_3$ is hydroxyl, and $R_1$, $R_2$, $R_4$, $R_5$ are independently hydrogen, hydroxyl or halogen. In another preferred embodiment, R is hydrogen, $R_3$ is hydroxyl, and $R_1$, $R_2$, $R_4$, $R_5$ are independently hydrogen or hydroxyl.

In an embodiment of the present invention, R is $C_{1-12}$ alkyl; preferably, R is $C_{1-11}$ alkyl; further preferably R is $C_{1-8}$ alkyl; most preferably, R is $C_{1-3}$ alkyl. Each carbon atom of the $C_{1-12}$ alkyl group may be optionally substituted with one to three substituents independently selected from hydroxyl, halogen, mercapto, $C_{1-6}$ alkyl, $C_{2-6}$ alkenyl, $C_{2-6}$ alkynyl, $C_{1-6}$ alkoxy, $C_{1-6}$ alkyl-(C=O)—, $C_{1-6}$ alkoxycarbonyl, $C_{3-6}$ cycloalkyl, $C_{3-6}$ cycloalkyl-methyl, $C_{2-6}$ heterocycloalkyl, $C_{2-6}$ heterocycloalkyl-methyl, $C_{6-10}$ aryl, $C_{6-10}$ aryloxy, $C_{5-10}$ heteroaryl, or $C_{5-10}$ heteroaryloxy. The carbon atoms of the R group may form linear, branched or cyclic structures.

In an embodiment, R is $C_{1-11}$ alkyl, $R_1$, $R_2$, $R_3$, $R_4$, $R_5$ are independently hydrogen, hydroxyl or halogen. In another embodiment, R is $C_{1-11}$ alkyl, $R_1$, $R_2$, $R_3$, $R_4$, $R_5$ are independently hydrogen or hydroxyl.

In a preferred embodiment, $R_1$, $R_2$, $R_3$, $R_4$, and $R_5$ together contain two or more hydroxyl groups, and further preferably contain three or more hydroxyl groups.

In an embodiment, the compounds of the invention are hydroxybenzoic acids. Preferably, the compounds are p-hydroxybenzoic acid, 2,3-dihydroxybenzoic acid, 2,4-dihydroxybenzoic acid, 3,4-dihydroxybenzoic acid, 4,5-dihydroxybenzoic acid, 4,6-dihydroxybenzoic acid, 2,3,4-trihydroxybenzoic acid, 3,4,5-trihydroxybenzoic acid, 3,4,6-trihydroxybenzoic acid, 3,5-dichloro-4-hydroxybenzoic acid, and 3-bromo-4-hydroxybenzoic acid.

In an embodiment, the compounds of the invention are hydroxybenzoic acid esters. Preferably, the compounds are p-hydroxybenzoic acid esters, 2,3-dihydroxybenzoic acid esters, 2,4-dihydroxybenzoic acid esters, 2,3,4-trihydroxybenzoic acid esters, 3,4,5-trihydroxybenzoic acid esters and 3,4,6-trihydroxybenzoic acid esters. Most preferably, the compounds are 3,4,5-trihydroxybenzoic acid esters and 3,4,6-trihydroxybenzoic acid esters.

In another embodiment, the compounds of the present invention include the following compounds: ethyl p-hydroxybenzoate, methyl 2,3-hydroxybenzoate, octyl 2,3-dihydroxybenzoate, methyl 2,4-dihydroxybenzoate, methyl 3,4-dihydroxybenzoate, methyl 2,3,4-trihydroxybenzoate, ethyl 2,3,4-trihydroxybenzoate, propyl 2,3,4-trihydroxybenzoate, octyl 2,3,4-tri hydroxybenzoate, methyl 3,4,5-trihydroxybenzoate, ethyl 3,4,5-trihydroxybenzoate, propyl 3,4,5-trihydroxybenzoate, octyl 3,4,5-trihydroxybenzoate, methyl 3,4,6-trihydroxybenzoate, ethyl 3,4,6-trihydroxybenzoate, propyl 3,4,6-trihydroxybenzoate, and octyl 3,4,6-trihydroxybenzoate.

The carbon atom content of the various hydrocarbon-containing moieties herein may be indicated by a prefix designating the minimum and maximum number of carbon atoms in the moiety, for example, the prefix $C_{a-b}$ alkyl indicates an alkyl moiety of the integer "a" to "b" carbon atoms, inclusive. Thus, for example, $C_{1-6}$ alkyl refers to an alkyl group of one to six carbon atoms inclusive.

The term "alkoxy" refers to straight or branched, monovalent, saturated aliphatic chains of carbon atoms bonded to an oxygen atom. Examples of alkoxy groups include methoxy, ethoxy, propoxy, butoxy, iso-butoxy, tert-butoxy, and the like.

The term "alkyl" refers to straight or branched, monovalent, saturated aliphatic chains of carbon atoms and includes, for example, methyl, ethyl, propyl, isopropyl, butyl, isobutyl, pentyl, isopentyl, hexyl, and the like.

The term "alkenyl" denotes a straight or branched-chain hydrocarbon having one or more double bonds and includes, for example, vinyl, propenyl, butenyl, isobutenyl, pentenyl, isopentenyl and the like.

The term "alkynyl" denotes a straight or branched-chain hydrocarbon having one or more triple bonds and includes, for example, ethynyl, propynyl, butynyl, isobutynyl, pentynyl, isopentynyl and the like.

The term "aryl" denotes a cyclic, aromatic hydrocarbon. Examples of aryl groups include phenyl, naphthyl, and the like.

The term "cycloalkyl" denotes a saturated monocyclic or polycyclic cycloalkyl group. Examples of cycloalkyl groups include cyclopropyl, cyclobutyl, cyclopentyl, cyclohexyl, and the like.

The term "halogen" represents chloro, bromo, fluoro, or iodo atoms.

The term "heteroaryl" denotes a monocyclic or polycyclic aromatic hydrocarbon group wherein one or more carbon atoms have been replaced with heteroatoms such as nitrogen, oxygen, or sulfur. If the heteroaryl group contains more than one heteroatom, the heteroatoms may be the same or different.

The term "heterocycloalkyl" denotes a saturated monocyclic or polycyclic cycloalkyl group, in which at least one of the carbon atoms have been replaced with a heteroatom such as nitrogen, oxygen, or sulfur. If the heterocycloalkyl group contains more than one heteroatom, the heteroatoms may be the same or different.

A cyclic group may be bonded to another group in more than one way. If no particular bonding arrangement is specified, then all possible arrangements are intended. For example, the term "pyridyl" includes 2-, 3-, or 4-pyridyl, and the term "thienyl" includes 2- or 3-thienyl.

The term "substituted" means that a hydrogen atom on a molecule has been replaced with a different atom or molecule. The atom or molecule replacing the hydrogen atom is denoted as a "substituent."

The compounds of the invention can be purchased on the market, extracted from natural materials or synthesized by known methods (see, for example, Jiang, P. et al., *Chemistry & Industry of Forest Products*, 2005, 25(B10), 113-115; Li, S. Q., *Hangzhou Chemical Industry*, 2002, 32(1), 25-26; Ling, C. X., *Chemical Industry Times*, 2006, 20(1), 25-26, 35; Zeng, Y. C. et al., *Guangzhou Chemical Industry and Technology*, 2005, 33(6), 13-17; Yu, S. X. et al., *Advances in Fine Petrochemicals*, 2002, 3(1), 42-45).

The compounds of this invention may be tested for their effect on virus infection using the real time quantitative fluorescent PCR to detect the amount of virus in a sample. This method has been reported in several publications (Youling Cai et al., *Prevention of Chinese Venereal Disease and Cancer*, 2002, 8: 2, 108; Yuansheng Wu, Ruiqiang, Qu, et al., *Practical Chinese and Western Medicine Clinics*, 2003, 3: 2, 1).

The compounds of the present invention and/or pharmaceutical compositions comprising such compounds are useful for preventing and/or treating virus infection such as HBV, papillomavirus and/or herpes virus infection as well as diseases related to virus infection in humans and animals.

Various diseases and disorders are found to be related to virus infection. For example, some acute or chronic liver diseases such as hepatitis B and cirrhosis and even hepatocyte cancers may be associated with HBV infection. Papillomaviruses infect the skin and mucous membranes of humans and animals and may cause lesions, abnormal cell growth or cancer in the infected subjects. Diseases or disorders that can be associated with human papillomavirus infection include, for example, anogenital and cutaneous warts, cervical, anal, perianal, vulvar, penile, skin, and oropharyngeal intraepithelial neoplasia, lesions and cancers. Tumors of the larynx and respiratory epithelium may be related to respiratory papillomas. Herpes virus infection may cause cold sores, encephalitis, genital herpes, vaginitis, cervicitis, cervical erosion, cervical cancer, chicken pox, shingles, post-herpetic neuralgia zoster multiplex, myelitis, herpes ophthalmicus, zoster sine herpete, and other related diseases.

In an embodiment, the present invention provides a method of killing or reducing the amount of virus in a sample by contacting the sample with an effective amount of a compound of the invention, preferably, the virus is HBV, papillomavirus or herpes virus, more preferably, the virus is HPV, including, without limitation, HPV subtypes 6, 11, 16 or 18. The effective amount of the compound for killing or reducing the amount of virus in a sample will vary according to the specific sample types and treatment conditions. It is readily determinable by one of ordinary skill in the art having benefit of the instant disclosure. In one embodiment, the effective amount of a compound of the invention for killing or reducing the amount of HBV, HPV or HSV virus in a sample is in the range of 0.1-20% (w/v), preferably, 1-15%, more preferably 3-10%.

In another embodiment, the present invention provides a method of killing or reducing the amount of virus in a subject by administering to the subject a pharmaceutically effective amount of a pharmaceutical composition comprising a compound of the invention, preferably, the virus is HBV, papillomavirus or herpes virus, more preferably, the virus is HPV, including, without limitation, HPV subtypes 6, 11, 16 or 18.

In another embodiment, the present invention provides a method of treating or alleviating virus infection in a subject by administering to such subject a pharmaceutically effective amount of a pharmaceutical composition comprising a compound of the invention, preferably, the virus is HBV, papillomavirus or herpes virus, more preferably, the virus is HPV, including, without limitation, HPV subtypes 6, 11, 16 or 18.

In another embodiment, the present invention provides a method of preventing virus infection in a subject by administering to the subject a pharmaceutically effective amount of a pharmaceutical composition comprising a compound of the invention, preferably, the virus is HBV, papillomavirus or herpes virus, more preferably, the virus is HPV, including, without limitation, HPV subtypes 6, 11, 16 or 18.

In another embodiment, the present invention provides a method of treating or alleviating hepatitis B, cirrhosis or hepatocyte cancer in a subject by administering to such subject a pharmaceutically effective amount of a pharmaceutical composition comprising a compound of the invention.

In another embodiment, the present invention provides a method of treating or alleviating skin or mucosal warts such as genital warts, flat warts and common warts, cervical, anal, perianal, vulvar, penile, skin or oropharyngeal intraepithelial neoplasia, lesions or cancers. In a preferred embodiment, the present invention provides a method of treating or alleviating cervical lesion or cervical cancer. In another embodiment, the present invention provides a method of preventing cervical lesion or cervical cancer in a subject by administering to the subject a pharmaceutically effective amount of a pharmaceutical composition comprising a compound of the invention.

In another embodiment, the invention provides a method for preventive treatment of asymptomatic infections of the cervix in patients identified by DNA diagnosis or suspected of HPV or HSV infection, or in patients who have undergone surgical treatment of cervical cancer, cervical intraepithelial neoplasia or squamous intraepithelial lesions. In another embodiment, the invention provides a method for preventive treatment in patients who have undergone surgical, laser or freeze removal of skin or mucosal warts.

In another embodiment, the present invention provides a method of treating or alleviating cold sores, encephalitis, genital herpes, vaginitis, chicken pox, shingles, post-herpetic neuralgia zoster multiplex, myelitis, herpes ophthalmicus, or zoster sine herpete. Preferably, the present invention provides a method of treating or alleviating cold sores, genital herpes, chicken pox or shingles.

The subject to be treated by the methods of the invention may be a human or an animal. In an embodiment, the subject is a human. In another embodiment, the subject is an animal, preferably, a chimpanzee, cattle, dog, rabbit, rat or bird.

In an embodiment, the present invention provides a pharmaceutical composition comprising a compound according to Formula (I), a stereoisomer or a prodrug thereof, or a pharmaceutically acceptable salt thereof together with a pharmaceutically acceptable excipient, carrier or diluent.

The phrase "pharmaceutically acceptable" indicates that the designated excipient, carrier or diluent is generally chemically and/or physically compatible with the other ingredients comprising the formulation, and physiologically compatible with the recipient thereof.

The term "pharmaceutically acceptable salts" refers to organic and inorganic salts of a compound of Formula (I). These salts can be prepared in situ during the final isolation and purification of a compound, or by separately reacting a compound of Formula (I) with a suitable organic or inorganic acid or base and isolating the salt thus formed. Representative salts include hydrobromide, hydrochloride, sulfate, bisulfate, nitrate, acetate, oxalate, besylate, palmitate, stearate, laurate, borate, benzoate, lactate, phosphate, tosylate, citrate, maleate, fumarate, succinate, tartrate, naphthylate, mesylate, glucoheptonate, lactobionate, laurylsulphonate salts, and the like. These may also include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. For additional examples see, for example, Berge, et al., J. Pharm. Sci., 66, 1-19 (1977), which is incorporated herein by reference.

The pharmaceutical composition of the invention may be administered to a subject through conventional administration routes, including without limitation, the oral, buccal, sublingual, ocular, topical, parenteral (e.g., intravenous, intramuscular, subcutaneous, intravascular or infusion), rectal, intracisternal, intravaginal, intraperitoneal, intravesical, inhalation or nasal methods.

Solid dosage forms for oral administration include, for example, capsules, tablets, powders, and granules. In such solid dosage forms, the active compound is admixed with at least one inert conventional pharmaceutical excipient (or carrier) such as sodium citrate or dicalcium phosphate, or (a) fillers or extenders, such as for example, starches, lactose, sucrose, mannitol, and silicic acid; (b) binders, such as for example, carboxymethyl-cellulose, alginates, gelatin, polyvinylpyrrolidone, sucrose, and acacia; (c) humectants, such as for example, glycerol; (d) disintegrating agents, such as for example, agar-agar, calcium carbonate, potato or tapioca starch, alginic acid, certain complex silicates, and sodium carbonate; (e) solution retarders, such as for example, paraffin; (f) absorption accelerators, such as for example, quaternary ammonium compounds; (g) wetting agents, such as for example, cetyl alcohol and glycerol monostearate; (h) adsorbents, such as for example, kaolin and bentonite; and/or (i) lubricants, such as for example, talc, calcium stearate, magnesium stearate, solid polyethylene glycols, sodium lauryl sulfate, or mixtures thereof. In the case of capsules and tablets, the dosage forms may further comprise buffering agents.

Solid dosage forms may be formulated as modified release and pulsatile release dosage forms containing excipients for immediate release dosage forms as described above together with additional excipients that act as release rate modifiers. Release rate modifiers include, but are not limited to, hydroxypropylmethyl cellulose, methyl cellulose, sodium carboxymethylcellulose, ethyl cellulose, cellulose acetate, polyethylene oxide, xanthan gum, ammonio methacrylate copolymer, hydrogenated castor oil, carnauba wax, paraffin wax, cellulose acetate phthalate, hydroxypropylmethyl cellulose phthalate, methacrylic acid copolymer and mixtures thereof. Modified release and pulsatile release dosage forms may contain one or a combination of release rate modifying excipients.

The pharmaceutical compositions of the invention may further comprise fast dispersing or dissolving dosage formulations (FDDFs) containing the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavouring, polyethylene glycol, fumed silica, silicon dioxide, sodium starch glycolate, sodium stearyl fumarate, sorbitol, xylitol. The terms dispersing or dissolving as used herein to describe FDDFs are dependent upon the solubility of the drug substance used i.e., where the drug substance is insoluble, a fast dispersing dosage form may be prepared, and where the drug substance is soluble, a fast dissolving dosage form may be prepared.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, benzyl benzoate, propylene glycol, 1,3-butylene glycol, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like. The liquid dosage forms may further include suspending agents, such as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Pharmaceutical compositions suitable for parenteral injection may comprise pharmaceutically acceptable sterile aqueous or nonaqueous solutions, dispersions, suspensions, or emulsions, and sterile powders for extemporaneous reconstitution into sterile injectable solutions or dispersions. Examples of suitable aqueous and nonaqueous carriers, vehicles, and diluents include water, ethanol, polyols (such as propylene glycol, polyethylene glycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions, and by the use of surfactants.

In an embodiment, the pharmaceutical compositions of the invention are administered topically. The topical formulations may be prepared in any form that is suitable for topical administration, including, without limitation, solutions, suspensions, emulsions, creams, ointments, gels, powders, liniments, salves and the like. If desired, these may be sterilized or mixed with auxiliary agents such as preservatives, stabilizers, wetting agents, buffers or salts for influencing osmotic pressure and the like. Preferred vehicles for semi-solid or solid form topical preparations include ointment bases such as polyethylene glycol-1000; conventional ophthalmic vehicles; creams such as HEB cream; and gels such as K-Y gel; as well as petroleum jelly and the like. These topical preparations may also contain emollients, perfumes, and/or pigments to enhance their acceptability for various usages.

Pharmaceutical compositions of the present invention may also be configured for treatments in veterinary use, where a compound of the present invention, or a veterinarily acceptable salt thereof, or veterinarily acceptable solvate or prodrug thereof, is administered as a suitably acceptable formulation in accordance with normal veterinary practice and the veterinary practitioner will determine the dosing regimen and route of administration which will be most appropriate for a particular animal.

In an embodiment, one or more compounds of the invention may be used in combination with one another. If a combination of active compounds is used, they may be administered simultaneously, separately or sequentially.

In another embodiment, one or more compounds of the invention may be used in combination with any other antiviral agents for treating, alleviating or preventing virus infection. Examples of antiviral agents include, without limitation, reverse transcriptase inhibitors such as Abacavir, Adefovir dipivoxil, Lamivudine, Stavudine, Tenofovir, Zidovudine, DNA polymerase inhibitors such as Acyclovir, Valacyclovir, Famciclovir, Penciclovir, Ganciclovir, Ribavirin, Foscarnet, Valganciclovir, Cidofovir, protease inhibitors such as Saquinavir, Nelfinavir, Indinavir, Ritonavir, Amprenavir, Fosamprenavir, Atazanavir, and other antiviral agents such as Aldara, CytoGam, Flumadine, Fuzeon and interferon.

In another embodiment, one or more compounds of the invention may be used in combination with one or more antifungal agents for treating or alleviating virus infection. Examples of antifungal agents include, without limitation, Terbinafine, Fluconazole, Ketoconazole, Miconazole, Itraconazole, Posaconazole, Virconazole, Polyene Macrolides, Amphotericin B, Griseofluvin, and Flucytosine.

In another embodiment, one or more compounds of the invention may be used in combination with one or more antibiotics for treating or alleviating virus infection. Examples of antibiotics include, without limitation, Amoxicillin, Ampicillin, Oxacillin, Azithromycin, Clarithromycin, Ciprofloxacin, Gemifloxacin, Cephalosporins, and Ceftizoxime.

In another embodiment, one or more compounds of the invention may be used in combination with one or more vaccines or immuno-modulators for preventing virus infection. In a preferred embodiment, one or more compounds of the invention may be used together with HBV or HPV vaccines to prevent HBV or HPV infection.

The dosage of the pharmaceutical compositions comprising the compounds of the invention can vary depending upon the age and mass of the subject being treated, the intended route of administration, the particular compound being administered, and the like. For example, a compound of the invention may be used as a micro emulsion for topical administration to a subject for treating or alleviating HPV or HSV infection at a dosage of 0.1-20% (w/v), preferably 1-15%, more preferably 3-10%. The determination of dosage ranges and optimal dosages for a particular subject is within the ability of one of ordinary skill in the art.

The compounds of this invention may also be included in personal care products to help prevent the spread of virus infection. Such personal care products include, without limitation, sterilization solutions, hand soaps, hand sanitizers, body cleansers, body cleansing gels, body washing soaps, personal care wipes, facial tissues and nasal sprays.

The pharmaceutical compositions and personal care products of this invention can be made with conventional methods known in the art.

EXAMPLES

The following examples are provided to further illustrate the present invention and are not to be interpreted as limiting the scope of the invention.

The materials used in the present invention and their suppliers are as follows:

| Materials | Suppliers |
| --- | --- |
| p-hydroxybenzoic acid | Sinopharm Chemical Reagent Co., Ltd. |
| Ethyl p-hydroxybenzoate | GuangZhou Gases Factory Co., Ltd. |
| 2,3-dihydroxybenzoic acid | Taizhou Zhongda Chemical Co., Ltd. |
| Methyl 2,3-dihydroxybenzoate | Taizhou Zhongda Chemical Co., Ltd. |
| 2,4-dihydroxybenzoic acid | Taizhou Zhongda Chemical Co., Ltd. |
| Methyl 2,4-dihydroxybenzoate | Taizhou Zhongda Chemical Co., Ltd. |
| 3,4-dihydroxybenzoic acid | Taizhou Zhongda Chemical Co., Ltd. |
| Methyl 3,4-dihydroxybenzoate | Taizhou Zhongda Chemical Co., Ltd. |
| 2,3,4-trihydroxybenzoic acid | Nanjing Longyuan Natural Polyphenol Synthesis Factory |
| Gallic acid | Zhejiang Ouhai Chemical Reagent Co. Ltd. |
| Propyl gallate | Lianyungang Hongqi Chemical Plant |
| Ethyl gallate | Nanjing Longyuan Natural Polyphenol Synthesis Factory |
| Methyl gallate | Nanjing Longyuan Natural Polyphenol Synthesis Factory |
| Octyl gallate | Nanjing Longyuan Natural Polyphenol Synthesis Factory |
| Dodecyl gallate | Nanjing Longyuan Natural Polyphenol Synthesis Factory |
| Recombinant human interferon $\alpha$-$2\beta$ gel | SIU-FUNG USTC Pharmaceutical Co., Ltd. |
| Polyinosinic-polycytidylic acid | Guangdong Kaiping Biochemical Pharmaceutical Co., Ltd. |
| 3,5-dicloro-4-hydroxybenzoic acid | A Johnson Matthey Company |
| 3-bromo-4-hydroxybenzoic acid | AYOCADO Research Chemicals Ltd. |

Example 1

Preparation of Anti-HPV Micro Emulsion 20 ml 1,2-propylene glycol, 15 ml Tween-80 and 5 ml azone were mixed together, proper amount of sterile distilled water was added to obtain 100 ml of solution for external use. 10 g each of benzoic acid, salicylic acid, a combination of benzoic acid and salicylic acid, p-hydroxybenzoic acid, 2,3-dihydroxybenzoic acid, 2,4-dihydroxybenzoic acid, 3,4-dihydroxybenzoic acid, ethyl p-hydroxybenzoate, methyl 3,4-dihydroxybenzoate, gallic acid, dodecyl gallate, octyl gallate, propyl gallate, ethyl gallate, methyl gallate, methyl 2,4-dihydroxybenzoate were added into 50 ml of the solution for external use, respectively. The pH value of the solution was adjusted to 5.5. Then proper amount of the solution for external use was added to obtain 100 ml micro emulsion containing 10% of one of the aforesaid compounds.

Example 2

Preparation of Anti-HBV Injection Solution Containing Propyl Gallate 10 g propyl gallate, 8.5 g sodium chloride, 10 ml 1,2-propylene glycol and 10 ml Tween-80 were mixed and dissolved in sterile distilled water to a final volume of 100 ml. The pH value of the solution was adjusted to 7.4. Then the solution was filtrated, encapsulated and sterilized at 100° C. for 30 minutes to obtain the injection solution of propyl gallate.

Example 3

Preparation of Tablets Containing Ethyl Gallate 0.25 g ethyl gallate, 0.01 g polyinosinic-polycytidylic acid and 0.45 g tartaric acid were sifted through an 80 mesh sieve separately, made into soft materials with 95% ethanol, and then sifted through a 12 mesh sieve. The obtained wet particles were dried at 50° C. 0.65 g sodium hydrogen carbonate, 0.02 g dextrin and sterile distilled water were mixed together to produce soft material, which was then sifted through a 12 mesh sieve and dried at 50° C. The obtained materials were mixed with the dried particles produced initially. Finally, sterile distilled water was added into the mixture, heated, mixed with 0.01 g PEG6000 and made into tablets.

Example 4

Drug Screening Through Quantitative Fluorescent PCR Analysis

Samples

The test compounds listed in Table 1 below were prepared as micro emulsions as described in Example 1. Saline water was used as the control.

Methyl 2,3,4-trihydroxybenzoate was prepared as follows: 10 g of 2,3,4-trihydroxybenzoic acid, 60 ml of methanol and 0.5 g of p-toluenesulfonic acid were added into a flask and microwaved at 510 W for 20 minutes. Then the remaining methanol was removed by distillation. The remnant after the distillation was dissolved in hot water and then cooled down to allow the product to crystallize out. The dissolution and crystallization steps were repeated once. Finally, the product in white powder form was obtained. The yield of the reaction was approximately 90%.

Propyl 2,3,4-trihydroxybenzoate was prepared by the same method as above except that 60 ml of propanol instead of methanol was used. The yield of the reaction was approximately 93%.

Octyl 2,3-dihydroxybenzoate was prepared as follows: 10 g of 2,3-dihydroxybenzoic acid, 30 ml of octanol and 0.5 g of p-toluenesulfonic acid were added into a flask and microwaved at 510 W for 20 minutes. Then the mixture was cooled down to allow the product to crystallize out. The mixture was filtered to collect the product and remove the extra octanol. The collected product was dissolved in hot water and then cooled down to allow the product to crystallize out again. The dissolution and crystallization steps were repeated one more time. Finally, the product in white powder form was obtained. The yield of the reaction was approximately 85%.

HPV samples: condyloma acuminata samples were taken from clinical patients. The samples were washed with saline water to wash away the blood. Then they were cut into pieces under sterile condition, mixed with three times volume of saline water, homogenized and stored at −40° C. for further use.

Experiment Methods

50 μl micro emulsion of each test compound or 50 μl of saline water was added into 50 μl homogenate of a HPV sample. The mixture was incubated in warm bath at 37° C. for 24 hours. Then the amount of HPV 6/11 and HPV 16/18 DNA was detected using FQ-PCR diagnostic kit purchased from Da An Gene Diagnostics Center. 0.2 ml DNA was extracted from each sample by conventional alkali cleavage method and put into a thin wall tube. Proper amount of primers, F-PROBE, DNTP, DNA Polymerase and buffer solutions were added to the tube. ABI PRISM™7700 quantitative fluorescent PCR machine was used. The reaction was conducted under the following conditions: initial denature at 93° C. for 2 minutes; further denature and anneal at 93° C. for 45 seconds and 55° C. for 120 seconds, repeat the cycle for 40 times. Finally, the result was analyzed and calculated by computer and shown in Table 1.

TABLE 1

Test result for drug screening by quantitative fluorescent PCR analysis of HPV

| Test compounds | HPV 6/11 Virus (copies/ml) | HPV 16/18 Virus (copies/ml) |
| --- | --- | --- |
| Control | $1.45 \times 10^6$ | $1.40 \times 10^5$ |
| Benzoic acid | $3.60 \times 10^5$ | $2.90 \times 10^4$ |
| Salicylic acid | $5.50 \times 10^5$ | $2.60 \times 10^4$ |
| Benzoic acid and Salicylic acid | $2.90 \times 10^5$ | $4.50 \times 10^4$ |
| p-dihydroxybenzoic acid | $7.00 \times 10^5$ | $1.30 \times 10^3$ |
| Ethyl p-dihydroxybenzoate | $8.50 \times 10^4$ | 0 |
| 3,4-dihydroxybenzoic acid | $1.90 \times 10^4$ | $8.50 \times 10^4$ |
| Methyl 3,4-dihydroxybenzoate | $8.50 \times 10^4$ | $6.00 \times 10^2$ |
| Gallic acid | 0 | 0 |
| dodecyl gallate | $6.70 \times 10^4$ | $4.90 \times 10^4$ |
| Octyl gallate | 0 | 0 |
| Propyl gallate | 0 | 0 |
| Ethyl gallate | 0 | 0 |
| Methyl gallate | 0 | 0 |
| 2,3,4-trihydroxybenzoic acid | 0 | 0 |
| Methyl 2,3,4-trihydroxybenzoate | 0 | 0 |
| Propyl 2,3,4-trihydroxybenzoate | 0 | 0 |
| 2,3-dihydroxybenzoic acid | $2.30 \times 10^4$ | $3.20 \times 10^3$ |
| Methyl 2,3-dihydroxybenzoate | $3.00 \times 10^4$ | $4.20 \times 10^2$ |
| Octyl 2,3-dihydroxybenzoate | $2.20 \times 10^2$ | $1.50 \times 10^2$ |
| 2,4-dihydroxybenzoic acid | $1.60 \times 10^4$ | $4.60 \times 10^3$ |
| Methyl 2,4-dihydroxybenzoate | $5.20 \times 10^4$ | $2.50 \times 10^2$ |
| 3,5-dicloro-4-hydroxybenzoic acid | $2.30 \times 10^3$ | $2.60 \times 10^4$ |
| 3-bromo-4-hydroxybenzoic acid | $3.40 \times 10^3$ | $5.00 \times 10^4$ |

Experiment Results 24 hours after adding the test compound, no HPV 6/11 or HPV 16/18 was detected by FQ-PCR when gallic acid, octyl gallate, propyl gallate, ethyl gallate, methyl gallate, 2,3,4-trihydroxybenzoic acid, methyl 2,3,4-trihydroxybenzoate or propyl 2,3,4-trihydroxybenzoate was tested. For the group of ethyl p-hydroxybenzoate, HPV 16/18 was not detected, either. The other hydroxybenzoic acids or esters tested could also reduce the amount of HPV as compared to the control group. The results showed that the compounds of the present invention could eliminate or reduce the amount of HPV effectively and rapidly in vitro.

Example 5

Clinical Use of Hydroxybenzoic Acid Ester in Treating Condyloma Acuminata

Diagnosis Standards

The following standards were taken from the Handbook for Venereal Disease Prevention and Treatment, the second edition, published by the Health and Epidemic Prevention Bureau of the Ministry of Health of the People's Republic of China.

Soft hyperplasia with nipple or cauliflower shaped or other shaped warts were found around the skin of the cunnus or anus. The result from 5% acetate acid white test was positive.

Patients Selection Standards

Patients selected for the clinical observation must meet the above standards. Plus the diameter of their skin lesions should equal to or be less than 1 cm. Additionally, the patients did not have any treatment for the disease in the two weeks before the observation. Patients who had vaginal yeast, trichomonas, bacteria infection or other complications, chronic diseases, serious liver or kidney diseases or women in pregnancy or lactation were not selected. Treatments to women would not be conducted in their menstrual periods.

Experiment Methods 50 qualified patients were selected and randomly divided into five groups to be tested with p-hydroxybenzoic acid, gallic acid, ethyl p-hydroxybenzoate, propyl gallate and recombinant human interferon α-2β gel, respectively. The samples of p-hydroxybenzoic acid, gallic acid, ethyl p-hydroxybenzoate and propyl gallate were prepared as described in Example 1. The patients were treated with the test sample to the affected areas three times a day, in the morning, at noon and night. The samples were applied to cover the warts and the patients were required to leave the treated areas exposed and not to move for 20 minutes.

Criteria for Treatment Effect

Observation time: 8 days. Patients not cured after 8 days would continue to use the test samples for another 12 weeks, and their prognosis was followed during the 12-week period. Observed items: the location, shape, size and number of warts were carefully observed and recorded before the treatment.
"Recovered": all skin lesions had disappeared;
"Obvious Effect": more than 70% of the skin lesions had disappeared;
"Improved": more than 30% of the skin lesions had disappeared;
"Not Effective": less than 30% of the skin lesions had disappeared or the original skin lesions didn't change or even enlarged.

The results showed that the recombinant human interferon α-2β gel which was regarded as the best drug in treating condyloma acuminata still took at least 4 weeks to eliminate the warts. When compared to recombinant human interferon α-2β gel, ethyl p-hydroxybenzoate, p-hydroxybenzoic acid, propyl gallate and gallic acid had more apparent treatment effect. Additionally, the compounds of the present invention did not cause any obvious skin irritation. The only side effect was that some patients might occasionally experience a burning sense when the compounds were used.

TABLE 2

Results of clinical use of compounds for treatment of condyloma acuminata

| | Recovered | | Obvious Effect | | Improved | Not Effective |
|---|---|---|---|---|---|---|
| | 1-4 days | 5-8 days | 1-4 days | 5-8 days | | |
| Gallic Acid | 2 | | 3 | 1 | 4 | |
| Propyl Gallate | 7 | 1 | 2 | | | |
| P-hydroxybenzoic Acid | | | | 5 | 2 | 3 |
| Ethyl p-hydroxybenzoate | 6 | 2 | 2 | | | |
| Recombinant Human Interferon α-2β Gel | The shortest period of treatment is 4 weeks | | | | | |

Example 6

Inhibition Effect of Hydroxybenzoic Acid Ester Analogue on Secretion of HBsAg and HBeAg by Hepatitis B 2.2.15 Cell Line Experiment Materials Hepatitis B 2.2.15 cell line was transfected by HBV DNA (purchased from Institute of Biochemistry and Cell Biology of Shanghai Institute for Biological Sciences or the National Center for Drug Screening) and used as the cell model for screening anti-HBV drug compounds (See *Chinese Journal Of Integrated Traditional and Western Medicine on Liver Diseases,* 2004, 14(3): 158). The cell culture medium DMEM (GIBCO Company), bovine serum (Hangzhou Siji Qing Biochemical Manufacturer), G418 (GIBCO Company), 3-(4,5-dimethylthiazol-2-yl)-2,5-diphenyltetrazoliumbromide (Sigma), HBsAg and HBeAg diagnostic kit (Shanghai Kehua Bio-engineering Co., Ltd).

Experiment Methods

The test compounds listed in Table 3 below were dissolved in a mixture containing 20 ml 1,2-propylene glycol and 15 ml Tween-80 and diluted with sterile saline water to 2 μmol/ml of the test compound. Then it was mixed with the cell culture medium at equal volume to obtain a solution containing 1 μmol/ml of the tested compound. Cells at the concentration of $1 \times 10^5$ cells per milliliter were inoculated to a 24-well plate at 1 ml/well. Supernatant from the cell culture mixture was collected three days later for testing. The results of inhibition rates of HBsAg and HBeAg were listed in Table 3.

Experiment Results

Gallic acid, propyl gallate, 3,4-dihydroxybenzoic acid, ethyl 3,4-dihydroxybenzoate had inhibition effect on the secretion of HBsAg and HBeAg by the 2.2.15 cells. Inhibition by propyl gallate and ethyl 3,4-dihydroxybenzoate was more effective than gallic acid and 3,4-dihydroxybenzoic acid.

TABLE 3

The effect of hydroxybenzoic acids and esters thereof on secretion of HBsAg and HBeAg by 2.2.15 cells

| Groups | HBsAg Inhibition rate | P value | HBeAg Inhibition Rate | P value |
|---|---|---|---|---|
| Control | 0 | | 0 | |
| Gallic Acid | 8.83% | <0.05 | 9.40% | <0.05 |
| Propyl Gallate | 18.83% | <0.01 | 12.04% | <0.05 |
| 3,4-dihydroxy-benzoic acid | 9.81% | <0.05 | 8.92% | <0.05 |

TABLE 3-continued

The effect of hydroxybenzoic acids and esters thereof on secretion of HBsAg and HBeAg by 2.2.15 cells

| Groups | HBsAg Inhibition rate | P value | HBeAg Inhibition Rate | P value |
|---|---|---|---|---|
| Ethyl 3,4-dihydroxybenzoate | 14.20% | <0.01 | 6.04% | <0.06 |

Note:
SPSS software was used for statistical analysis and the T test

Example 7

External Treatment of HSV Infection in Clinical Tests

Twenty-two patients who were clinically diagnosed with HSV infection were randomly selected and divided into two groups. Acyclovir ointment and micro emulsion containing propyl gallate prepared as described in Example 1 were applied to the two groups, respectively, on the affected areas of the patients three times a day.

The results showed that the average time for recovery by using propyl gallate was 3 days while the average time for recovery for treatment with the acyclovir ointment was 5.5 days. The propyl gallate micro emulsion was more effective than the acyclovir ointment in treating HSV infection.

The same test was conducted with gallic acid. The average time for recovery by using gallic acid was also 3 days.

Example 8

Preparation of Liquid Hand Cleanser

Myristyl sodium sulfate, 1,2-propylene glycol, 4-chloro-3,5-dimethylphenol, triclosan and fragrance material were mixed together according to the ratio listed in Table 4 below and water was added to the mixture to make a final solution containing 5% water. Then the mixture was heated to 80° C. with stirring until the ingredients were fully dissolved. The resultant solution was cooled to room temperature. Ethyl p-hydroxybenzoate or gallic acid was added and dissolved in the solution with stirring. The pH value of the solution was adjusted to 5.0 with NaOH or HCl. Then sterile distilled water was added to obtain a product containing either ethyl p-hydroxybenzoate or gallic acid as the antiviral compound.

TABLE 4

Preparation of liquid hand cleanser

| Ingredients (wt. %) | 6 | 7 | 8 | 9 | 10 |
|---|---|---|---|---|---|
| Myristyl sodium sulfate | — | 5.00 | 5.00 | — | 5.00 |
| 1,2-propylene glycol | 20.00 (V/V) | 20.00 (V/V) | 20.00 (V/V) | 20.00 (V/V) | 20.00 (V/V) |
| Ethyl p-hydroxybenzoate or gallic acid | 1.00 | 5.00 | 8.00 | 4.00 | — |
| NaOH/HCl | To pH 5.0 | To pH 4.5 | To pH 4.0 | To pH 6.5 | To pH 6.0 |
| 4-chloro-3,5-dimethylphenol | 1.50 | — | — | — | — |
| Triclosan | — | 0.25 | 1.00 | — | 1.00 |
| Fragrance material | 1.0 | 1.0 | — | 1.0 | 1.0 |
| Sterile distilled water | To 100% | To 100% | To 100% | To 100% | To 100% |

Example 9

Stability Test of Propyl Gallate and Gallic Acid 20 ml 1,2-propylene glycol, 15 ml Tween-80 and 5 ml azone were mixed together and sterile distilled water was added to bring the volume to 100 ml. The pH value of the solution was adjusted to pH 6.8 with NaOH or HCl to obtain a micro emulsion. 10 g propyl gallate and 10 g gallic acid were dissolved in the micro emulsion, respectively, and mixed well. 10 ml of each micro emulsion was added to a capped transparent glass tube. Both solutions were colorless. The absorbance of the two solutions at 400~500 nm was measured with spectrophotometry and their absorbance was under 0.15. After the two solutions were kept at room temperature for 30 days, the gallic acid solution changed to light brown while the propyl gallate solution remained colorless. Measured by spectrophotometry again, the absorbance of the gallic acid solution was 1.2 and that of the propyl gallate solution was 0.4. It showed that propyl gallate was more stable in solution than gallic acid.

Example 10

Clinical Use of Hydroxybenzoic Acid Ester in Treating Flat Warts

Preparation of Propyl Gallate Micro Emulsion 5 g propyl gallate was mixed with 40 ml 1,2-propylene glycol and heated to dissolve the ingredients. Then 20 ml Tween-80 and 3 ml azone were added into the mixture and mixed well. Sterile distilled water was added to the mixture to reach a final volume of 100 ml.

Diagnosis Standards and Patient Selection

Clinically, flat warts were seen as slightly raised, smooth, tan or flesh colored bumps ranging in size from 1-5 mm. They typically appeared on the face, backs of hands and arms.

32 male and 28 female patients of 15-46 years old, with the average age of 23 years old, were selected for the test. These patients have had flat warts for any time from 2 weeks to 2 years. Some of the patients have tried other treatment methods for the warts. But no one had undertaken any treatment for the warts in the past 4 weeks. And no one had taken any medicine in the past 2 weeks.

Experiment Methods

The patients were randomly divided into two groups of 30 patients each. One group was treated with propyl gallate micro emulsion, the other group with 5% imiquimod cream (made by Sichuan Ming Xin Pharmaceutical Co.), which is a medicine often used for treating flat warts. The test samples were applied to the affected areas of the patient groups three times a day, in the morning, at noon and night. The treatment period was 20 days. The treatment effect was tracked for one year.

Criteria for Treatment Effect

"Recovered": all warts had disappeared or faded, the skin became flat, no new warts appeared;

"Obvious Effect": more than 70% of the warts had disappeared, the bottom of the warts had shrunk, the top of the warts had flattened;

"Improved": more than 30% of the warts had disappeared, the top of the warts had flattened;

"Not Effective": less than 30% of the warts had disappeared, no change to the warts, or some new warts appeared.

The effectiveness of treatment was calculated based on the number of patients that were "recovered" or showed "obvious effect". The results were shown in Table 5 below.

TABLE 5

Test results of using propyl gallate to treat flat warts.

|  | Recovered | Obvious Effect | Improved | Not Effective | Effective Rate |
|---|---|---|---|---|---|
| Propyl Gallate | 22 | 5 | 2 | 1 | 90% |
| 5% Imiquimod Cream | 11 | 10 | 4 | 5 | 70% |
|  |  |  |  |  | P ≦ 0.05 |

The results showed that propyl gallate was more effective than the 5% imiquimod cream in treating flat warts. The "recovered" patients were followed for a year and none had recurrence of the warts.

Example 11

Clinical Use of Propyl Gallate in Treating Cervical Erosion

Preparation of Propyl Gallate Micro Emulsion 4 g propyl gallate was mixed with 40 ml 1,2-propylene glycol and heated to let the ingredients to dissolve. Sterile distilled water was added to the mixture to reach a final volume of 100 ml.

Patient Selection 28 married female patients of 22-50 years old were selected for the test. Cervical tissue samples were taken from these patients before the test to make sure that they did not exhibit pathological changes of cervical epithelial neoplasia or cervical cancer. The patients were also tested for the absence of vaginal yeast infection or trichomoniasis or sexually transmitted diseases.

Experiment Methods

The patients were randomly divided into two groups of 14 patients each. One group was treated with propyl gallate micro emulsion, the other group with interferon-α suppository (made by Wuhan Tian'ao Pharmaceutical Co.). The treatment was started three days after a patient's last menstrual period. The propyl gallate micro emulsion was applied to the mucosa surfaces with cervical erosion every other day for 30 days. Out of the group treated with propyl gallate, 7 patients had the medicine applied to them by medical professionals at a hospital, the other 7 patients applied the medicine by themselves at home. On the other hand, an interferon-α suppository was used by each patient in the control group once a day before sleep for 30 days.

Criteria for Treatment Effect

"Recovered": the cervical skin became smooth, cervical erosion had disappeared;

"Improved": the cervical erosion surface shrank by more than 50% in size; severe erosion was changed to medium erosion; medium erosion was changed to slight erosion; nipple shaped erosion was changed to granule shaped; or granule shaped was changed to simple shaped;

"Not Effective": the cervical erosion surface change was less than 50% in size or there was no change in the erosion surface size.

The effectiveness of treatment was calculated based on the number of patients that were "recovered" or "improved". Among patients of the propyl gallate group who were treated at the hospital, the "recovered" rate was about 81%, the "improved" rate was about 15%, and the total effectiveness rate was about 96%. Among patients of the propyl gallate group who were treated at home, the "recovered" rate was about 32%, the "improved" rate was about 55%, and the total effectiveness rate was about 87%. Among patients treated with interferon-α suppository, the "recovered" rate was about 22%, the "improved" rate was about 57%, and the total effectiveness rate was about 79%. The effectiveness of propyl gallate treatment among patients treated at the hospital was significantly better than that of the interferon-α suppository (P<0.05). The reason that the effectiveness of propyl gallate treatment was lower in patients treated at home could be that the patients did not apply the medicine properly to the erosion surfaces.

The invention claimed is:

1. A method of treating or alleviating virus infection in a subject comprising administering to the subject a pharmaceutically effective amount of a pharmaceutical composition consisting essentially of a compound having the structure of Formula (I) below:

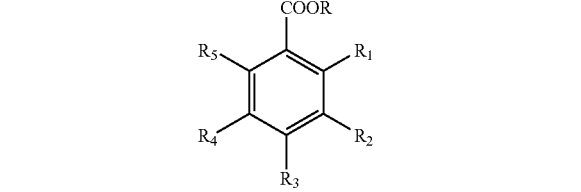

Wherein, R is hydrogen or $C_{1-11}$ alkyl; $R_1$, $R_2$, $R_3$, $R_4$, $R_5$ are independently hydrogen, halogen, hydroxyl, mercapto, $C_{1-6}$ alkyl, $C_{2-6}$ alkenyl, $C_{2-6}$ alkynyl, $C_{1-6}$ alkoxy, $C_{1-6}$ alkyl-(C=O)—, $C_{1-6}$ alkoxycarbonyl, $C_{3-6}$ cycloalkyl, $C_{3-6}$ cycloalkyl-methyl, $C_{2-6}$ heterocycloalkyl, $C_{2-6}$ heterocycloalkyl-methyl, $C_{6-10}$ aryl, $C_{6-10}$ aryloxy, $C_{5-10}$ heteroaryl, or $C_{5-10}$ heteroaryloxy, and at least three of $R_1$, $R_2$, $R_3$, $R_4$, and $R_5$ are hydroxyl; and wherein the virus infection is papilloma virus infection.

2. The method of claim 1 wherein R is $C_{1-8}$ alkyl.

3. The method of claim 2 wherein R is $C_{1-3}$ alkyl.

4. The method of claim 1 wherein $R_1$, $R_2$, $R_3$, $R_4$ and $R_5$ are independently hydrogen, hydroxyl or halogen, and at least three of which are hydroxyl.

5. The method of claim 4 wherein $R_1$, $R_2$, $R_3$, $R_4$ and $R_5$ are independently hydrogen or hydroxyl.

6. The method of claim 2 wherein $R_1$, $R_2$, $R_3$, $R_4$ and $R_5$ are independently hydrogen, hydroxyl or halogen, and at least three of which are hydroxyl.

7. The method of claim 6 wherein $R_1$, $R_2$, $R_3$, $R_4$ and $R_5$ are independently hydrogen or hydroxyl.

8. The method of claim 3 wherein $R_1$, $R_2$, $R_3$, $R_4$ and $R_5$ are independently hydrogen, hydroxyl or halogen, and at least three of which are hydroxyl.

9. The method of claim 8 wherein $R_1$, $R_2$, $R_3$, $R_4$ and $R_5$ are independently hydrogen or hydroxyl.

10. The method of claim 1 wherein said compound is selected from the group consisting of 2,3,4-trihydroxybenzoic acid, 3,4,5-trihydroxybenzoic acid, 2,4,5-trihydroxybenzoic acid, 2,3,4-trihydroxybenzoic acid ester, 3,4,5-trihydroxybenzoic acid ester and 3,4,6-trihydroxybenzoic acid ester.

11. The method of claim 10 wherein said compound is selected from the group consisting of 3,4,5-trihydroxybenzoic acid, 2,3,4-trihydroxybenzoic acid ester, 3,4,5-trihydroxybenzoic acid ester and 3,4,6-trihydroxybenzoic acid ester.

12. The method of claim 1 wherein the virus is human papilloma virus (HPV).

13. The method of claim 12 wherein the virus is HPV subtypes 6, 11, 16 or 18.

14. The method of claim 1 wherein the subject is a human or an animal.

15. The method of claim 1 wherein the pharmaceutical composition is administered by the oral, topical, parenteral, rectal, intravaginal, inhalation or nasal method.

16. The method of claim 15, wherein the pharmaceutical composition is administered by the topical, rectal and intravaginal method.

17. The method of claim 15, wherein the pharmaceutical composition is administered by the intravenous method.

18. A method of treating or alleviating a disease in a subject comprising administering to the subject a pharmaceutically effective amount of a pharmaceutical composition consisting essentially of a compound having the structure of Formula (I) below:

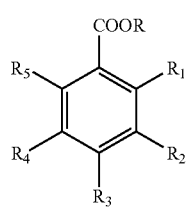

(I)

Wherein, R is hydrogen or $C_{1-11}$ alkyl; $R_1$, $R_2$, $R_3$, $R_4$, $R_5$ are independently hydrogen, halogen, hydroxyl, mercapto, $C_{1-6}$ alkyl, $C_{2-6}$ alkenyl, $C_{2-6}$ alkynyl, $C_{1-6}$ alkoxy, $C_{1-6}$ alkyl-(C=O)—, $C_{1-6}$ alkoxycarbonyl, $C_{3-6}$ cycloalkyl, $C_{3-6}$ cycloalkyl-methyl, $C_{2-6}$ heterocycloalkyl, $C_{2-6}$ heterocycloalkyl-methyl, $C_{6-10}$ aryl, $C_{6-10}$ aryloxy, $C_{5-10}$ heteroaryl, or $C_{5-10}$ heteroaryloxy, and at least three of $R_1$, $R_2$, $R_3$, $R_4$ and $R_5$ are hydroxyl; and wherein the disease is cervical diseases, skin or mucosal warts and is associated with HPV infection.

19. The method of claim 18 wherein said compound is selected from the group consisting of 2,3,4-trihydroxybenzoic acid, 3,4,5-trihydroxybenzoic acid, 2,4,5-trihydroxybenzoic acid, 2,3,4-trihydroxybenzoic acid ester, 3,4,5-trihydroxybenzoic acid ester and 3,4,6-trihydroxybenzoic acid ester.

20. The method of claim 19 wherein said compound is selected from the group consisting of 3,4,5-trihydroxybenzoic acid, 2,3,4-trihydroxybenzoic acid ester, 3,4,5-trihydroxybenzoic acid ester and 3,4,6-trihydroxybenzoic acid ester.

21. A method of killing or reducing the amount of virus in a sample comprising contacting said sample with an effective amount of a composition consisting essentially of a compound having the structure of Formula (I) below:

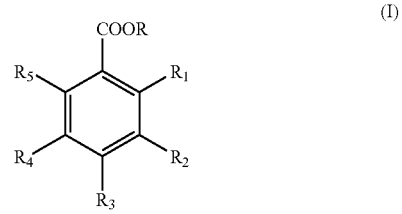

(I)

Wherein, R is hydrogen or $C_{1-11}$ alkyl; $R_1$, $R_2$, $R_3$, $R_4$, $R_5$ are independently hydrogen, halogen, hydroxyl, mercapto, $C_{1-6}$ alkyl, $C_{2-6}$ alkenyl, $C_{2-6}$ alkynyl, $C_{1-6}$ alkoxy, $C_{1-6}$ alkyl-(C=O)—, $C_{1-6}$ alkoxycarbonyl, $C_{3-6}$ cycloalkyl, $C_{3-6}$ cycloalkyl-methyl, $C_{2-6}$ heterocycloalkyl, $C_{2-6}$ heterocycloalkyl-methyl, $C_{6-10}$ aryl, $C_{6-10}$ aryloxy, $C_{5-10}$ heteroaryl, or $C_{5-10}$ heteroaryloxy, and at least three of $R_1$, $R_2$, $R_3$, $R_4$, and $R_5$ are hydroxyl; and wherein the virus is papillomavirus.

22. The method of claim 21 wherein said compound is selected from the group consisting of 2,3,4-trihydroxybenzoic acid, 3,4,5-trihydroxybenzoic acid, 2,4,5-trihydroxybenzoic acid, 2,3,4-trihydroxybenzoic acid ester, 3,4,5-trihydroxybenzoic acid ester and 3,4,6-trihydroxybenzoic acid ester.

23. The method of claim 22 wherein said compound is selected from the group consisting of 3,4,5-trihydroxybenzoic acid, 2,3,4-trihydroxybenzoic acid ester, 3,4,5-trihydroxybenzoic acid ester and 3,4,6-trihydroxybenzoic acid ester.

* * * * *